United States Patent

Herzig et al.

[11] Patent Number: 5,939,579
[45] Date of Patent: Aug. 17, 1999

[54] DISPERSE DYES

[75] Inventors: Paul Herzig; Antoine Clément; Alfons Arquint, all of Basel, Switzerland

[73] Assignee: Ciba Specialty Chemicals Corporation, Tarrytown, N.Y.

[21] Appl. No.: 09/110,595

[22] Filed: Jul. 6, 1998

[30] Foreign Application Priority Data

Jul. 15, 1997 [CH] Switzerland ............ 1725/97

[51] Int. Cl.$^6$ .................................................. C07C 233/43
[52] U.S. Cl. .......................................................... 560/43
[58] Field of Search ............... 534/854; 560/43; 8/693, 922

[56] References Cited

U.S. PATENT DOCUMENTS

| | | | |
|---|---|---|---|
| 2,373,700 | 4/1945 | McNally et al. | 534/854 X |
| 3,178,405 | 4/1965 | Merian et al. | 534/854 |
| 4,210,586 | 7/1980 | Clark et al. | 534/854 |
| 4,389,531 | 6/1983 | Clark | 560/43 |
| 5,550,217 | 8/1996 | Trottmann | 534/732 |
| 5,723,587 | 3/1998 | Clément et al. | 534/854 |

FOREIGN PATENT DOCUMENTS 58-152056  9/1983  Japan .

OTHER PUBLICATIONS

Derwent Abstract of JP 58–152,056, Sep. 9, 1993.

*Primary Examiner*—Fiona T. Powers
*Attorney, Agent, or Firm*—Kevin T. Mansfield; Jacob M. Levine; David R. Crichton

[57] ABSTRACT

Disperse dyes of formula

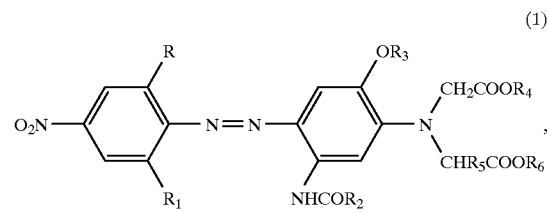

(1)

wherein R is nitro or cyano, $R_1$ is halogen, $R_2$ is $C_1$–$C_4$alkyl which is unsubstituted or substituted by $C_1$–$C_3$alkoxy, halogen, cyano or phenyl, $R_3$ is $C_1$–$C_4$alkyl, $R_4$ is methyl or ethyl, $R_5$ is hydrogen, methyl or ethyl, and $R_6$ is methyl or ethyl, with the proviso that $R_5$ is not hydrogen if R is nitro, $R_1$ is halogen and $R_2$ is $C_1$–$C_4$alkyl.

These dyes are particularly suitable for dyeing and printing textile materials consisting of polyester fibres.

2 Claims, No Drawings

DISPERSE DYES

The present invention relates to disperse dyes, to a process for their preparation as well as to their use for dyeing or printing semi-synthetic or synthetic hydrophobic fibre materials.

Disperse dyes, i.e. dyes which do not contain any water-solubilising groups, have been known for a long time and are used for dyeing hydrophobic textile materials. Often, however, the resultant dyeings are not sufficiently fast to thermomigration and some of their properties are also unsatisfactory, in particular their fastness to washing and perspiration. This problem occurs in particular with blue and navy blue shades.

This invention relates to disperse dyes with which dyeings are obtained that are very fast to thermomigration as well as to washing and perspiration and which in addition have good build-up in the exhaust and thermosol processes as well as in textile printing. The dyes are also suitable for discharge printing.

The novel dyes correspond to formula $$\text{(1)}$$

[structure with $O_2N$, $R$, $R_1$, $N=N$, $OR_3$, $CH_2COOR_4$, $CHR_5COOR_6$, $NHCOR_2$]

wherein
R is nitro or cyano,
$R_1$ is halogen,
$R_2$ is $C_1$–$C_4$alkyl which is unsubstituted or substituted by $C_1$–$C_3$alkoxy, halogen, cyano or phenyl,
$R_3$ is $C_1$–$C_4$alkyl,
$R_4$ is methyl or ethyl,
$R_5$ is hydrogen, methyl or ethyl, and
$R_6$ is methyl or ethyl, with the proviso that $R_5$ is not hydrogen if R is nitro, $R_1$ is halogen and $R_2$ is $C_1$–$C_4$alkyl.

$R_1$ defined as halogen is bromo, chloro or iodo.
$R_2$ and $R_3$ defined as $C_1$–$C_4$alkyl are each independently of the other typically methyl, ethyl, n-propyl, isopropyl, n-butyl, sec-butyl, tert-butyl and isobutyl.
$R_1$ is chloro or bromo. Chloro is preferred.
$R_2$ is ethyl or methyl. Methyl is preferred.
$R_3$ is ethyl or methyl. Methyl is preferred.
$R_5$ is hydrogen or methyl. Methyl is preferred.

The dyes of formula (1) can be prepared by processes which are known per se. They are obtained, for example, by diazotising a compound of formula $$\text{(2)}$$

[structure with $O_2N$, $R$, $R_1$, $NH_2$]

and coupling the diazonium compound so obtained to a coupling component of formula $$\text{(3)}$$

[structure with $OR_3$, $CH_2COOR_4$, $CHR_5COOR_6$, $NHCOR_2$]

R, $R_1$, $R_2$, $R_3$, $R_4$, $R_5$ and $R_6$ having the meanings given for formula (1).

The diazotisation of the compounds of formula (2) is carried out in per se known manner, for example with sodium nitrite in acid, typically hydrochloric or sulfuric acid, aqueous medium. The diazotisation can, however, also be carried out with other diazotising agents, conveniently with nitrosylsulfuric acid. The reaction medium of the diazotisation may contain an additional acid, typically phosphoric acid, sulfuric acid, acetic acid, propionic acid, hydrochloric acid or mixtures of these acids, for example mixtures of phosphoric acid and acetic acid. The diazotisation is conveniently carried out in the temperature range from –10 to 30° C., preferably from –10° C. to room temperature.

The coupling of the diazotised compounds of formula (2) to the coupling component of formula (3) is likewise carried out in known manner, conveniently in acid, aqueous or aqueous-organic medium, preferably in the temperature range from –10 to 30° C., most preferably below 10° C. Suitable acids include hydrochloric acid, acetic acid, sulfuric acid or phosphoric acid. Diazotisation and coupling may be typically carried out in the same reaction medium.

Some of the diazo components of formula (2) and the coupling components of formula (3) are known or can be prepared in per se known manner.

The coupling component of formula $$\text{(3a)}$$

[structure with $OCH_3$, $CH_2COOR_4$, $CH(CH_3)COOR_6$, $NHCOCH_3$]

wherein $R_4$ and $R_6$ have the meaning given for formula (1) are novel and are also an object of this invention.

The coupling component of formula (3a) is prepared, for example, by reacting 3-amino-4-methoxyacetanilide first with a compound of formula $CH_3$—CHCl—$COOR_6$ and then with a compound of formula $CH_2Cl$—$COOR_4$.

The novel dyes of formula (1) can be used for dyeing and printing semi-synthetic and, preferably, synthetic hydrophobic fibre materials, in particular textile materials. Textile materials made from blends that contain such semi-synthetic or synthetic hydrophobic fibre materials can also be dyed or printed with the novel dyes.

Suitable semi-synthetic textile materials are in particular cellulose secondary acetate and cellulose triacetate.

Synthetic hydrophobic textile materials consist primarily of linear aromatic polyesters, typically those of terephthalic acid and glycols, especially ethylene glycol, or of condensates of terephthalic acid and 1,4-bis(hydroxymethyl) cyclohexane; of polycarbonates, typically those of α,α-dimethyl-4,4'-dihydroxydiphenylmethane and phosgene, or of fibres based on polyvinyl chloride and polyamide.

The novel dyes are applied to the textile materials by known dyeing methods. Typically, polyester fibre materials are dyed from an aqueous dispersion by the exhaust process in the presence of customary anionic or nonionic dispersants and in the presence or absence of customary swelling agents (carriers) in the temperature range from 80 to 140° C. Cellulose secondary acetate is preferably dyed at a temperature from about 65 to 85° C., and cellulose triacetate at temperatures of up to 115° C.

The novel dyes do not stain wool and cotton simultaneously present in the dyebath or effect only minor staining (very good resist), so that they can also readily be used for dyeing polyester/wool and polyester/cellulose blends.

The novel dyes are suitable for dyeing by the thermosol process, for exhaust and continuous processes and for printing. The exhaust dyeing process is preferred. The liquor ratio depends on the apparatus used, on the substrate and on the form of presentation. However, it may be chosen from a wide range, e.g. from 1:4 to 1:100, but is preferably from 1:6 to 1:25.

The cited textile material can be in any form of presentation, such as fibre, thread or non-woven fabric, or wovens or knitgoods.

It is expedient to convert the novel dyes, before use, into a dye formulation. This is done by milling the dye to an average particle size of 0.1 to 10 micron. Milling can be carried out in the presence of dispersants. Typically, the dried dye is milled with a dispersant, or kneaded in paste form with a dispersant, and thereafter dried under vacuum or by spray drying. Printing pastes and dyebaths can be prepared by adding water to the formulations so obtained.

This invention also relates to dye formulations, which comprise a) as dye component 30 to 50% by weight, based on the total weight of the dye formulation, of a dye of formula

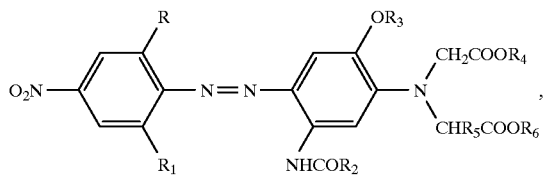

(1)

wherein R is nitro or cyano, $R_1$ is halogen, $R_2$ is $C_1$–$C_4$alkyl which is unsubstituted or substituted by $C_1$–$C_3$alkoxy, halogen, cyano or phenyl, $R_3$ is $C_1$–$C_4$alkyl, $R_4$ is methyl or ethyl, $R_5$ is hydrogen, methyl or ethyl, and $R_6$ is methyl or ethyl, and b) 50 to 70% by weight, based on the total weight of the dye composition, of a dispersant.

Suitable dispersants are, for example, anionic dispersants, such as aromatic sulfonic acid/formaldehyde condensates, sulfonated creosote oil/formaldehyde condensates, lignin sulfonates or copolymers of acrylic acid derivatives and of styrene derivates, preferably aromatic sulfonic acid/formaldehyde condensates or lignin sulfonates, or nonionic dispersants based on polyalkylene oxides obtainable, for example, by polyaddition reaction from ethylene oxide or propylene oxide.

The dye formulations of this invention are preferably solid.

The novel dye formulations are distinguished by being readily convertable into the form in which they can be applied, for example into the finished printing paste or dye baths.

The customary thickeners will be used for printing, for example modified or unmodified natural products, typically alginates, British gum, gum arabic, crystal gum, carob bean gum, tragacanth, carboxymethylcellulose, hydroxyethylcellulose, starch or synthetic products, typically polyacrylamides, polyacrylic acids or their copolymers, or polyvinyl alcohols.

The novel dyes impart to the cited materials, especially to the polyester material, level blue to navy blue shades of very good end-use properties, such as good fastness to light and sublimation. To be mentioned in particular is the excellent fastness to washing and perspiration and, especially, to thermomigration. The novel dyes are furthermore distinguished by good exhaustion and build-up.

The novel dyes can also be very well used for the preparation of mixed shades with each other or also together with other dyes.

This invention relates to the above-mentioned uses of the novel dyes as well as to a process for dyeing or printing semi-synthetic or synthetic hydrophobic fibre material, in particular textile material, which process comprises applying to, or incorporating into, the cited material one or more than one of the novel dyes. The cited hydrophobic fibre material is preferably textile polyester material. Other substrates which can be treated with the process of this invention as well as preferred process conditions are to be found above in the detailed description of the use of the novel dyes.

In another of its aspects, this invention relates to the hydrophobic fibre material, preferably polyester textile material, dyed or printed by the cited process.

The novel dyes of formula (1) are also suitable for modern recording processes such as thermotransfer printing.

The invention is illustrated by the following Examples. Unless otherwise stated, parts and percentages are by weight and the temperatures are given in degrees Celsius. The relationship between parts by weight and parts by volume is the same as that between the gramme and the cubic centimeter.

EXAMPLE 1

In a reaction flask, 60.0 parts by weight of 3-amino-4-methoxyacetanilide are added to 200 parts by weight of methyl chloroacetate at a temperature from 20 to 30° C. To this mixture are then added 60 parts by weight of sodium carbonate. The resulting suspension is evenly heated, with constant stirring, to 115° C. and is kept for 6 hours at this temperature. After the reaction is complete, the mixture is cooled to room temperature, charged with 330 parts by weight of water and stirred for 30 minutes until the salts are completely dissolved. After being stood for a short period, 2 phases form in the reaction flask. The lower, organic, phase is isolated and excess methyl chloroacetate is removed therefrom by distillation in a rotary evaporator. This gives 105 parts by weight of the compound of formula

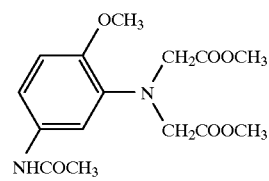

(10)

in the form of a resinous residue which is then dissolved in 195 parts by weight of acetic acid.

EXAMPLE 2

In a reaction flask, 72.6 parts by weight of 2-amino-3-bromo-5-nitrobenzonitrile are dissolved in 107 parts by weight of 98% sulfuric acid at a maximum temperature of 35° C. 104 parts by weight of 40% nitrosylsulfuric acid are added dropwise over 40 minutes to this reaction mixture which is then stirred for 120 minutes at 25° C. The resultant diazo solution is then added dropwise to 300 parts by weight of the 35% solution of the coupling component of Example 1 and to 200 parts by weight of ice over 60 minutes at 0 to 5° C., the reaction temperature being kept at a maximum of 5° C. by addition of ice. After addition of the diazo solution is complete, the mixture is stirred for 2 hours, the temperature rising to 20° C. The resultant precipitate is collected by filtration, washed with water and dried, giving 153 parts by weight of a dye of formula

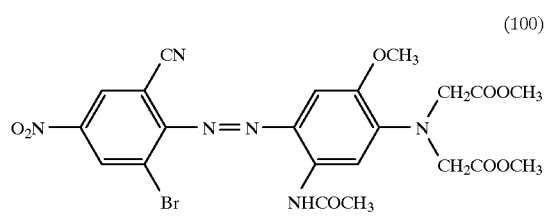

(100)

which dyes polyester textile material in a blue shade having good fastness properties, in particular good fastness to thermomigration and washing.

EXAMPLES 3–22

The dyes of formulae (101) to (120) listed in Table 1 can be prepared in general analogy to the instructions of Example 2. They also dye polyester textile material in navy blue and blue shades having good fastness properties, in particular good fastness to thermomigration and washing.

TABLE 1

| Ex. No./formula No. | R | $R_1$ | $R_4$ | $R_5$ | $R_6$ | Shade |
|---|---|---|---|---|---|---|
| 3/(101) | $NO_2$ | Br | $CH_3$ | $CH_3$ | $CH_3$ | navy blue |
| 4/(102) | $NO_2$ | Br | $CH_2CH_3$ | $CH_3$ | $CH_3$ | navy blue |
| 5/(103) | $NO_2$ | Br | $CH_3$ | $CH_3$ | $CH_2CH_3$ | navy blue |

TABLE 1-continued

| Ex. No./formula No. | R | $R_1$ | $R_4$ | $R_5$ | $R_6$ | Shade |
|---|---|---|---|---|---|---|
| 6/(104) | $NO_2$ | Br | $CH_2CH_3$ | $CH_3$ | $CH_2CH_3$ | navy blue |
| 7/(105) | $NO_2$ | Cl | $CH_3$ | $CH_3$ | $CH_3$ | navy blue |
| 8/(106) | $NO_2$ | Cl | $CH_3$ | $CH_3$ | $CH_2CH_3$ | navy blue |
| 9/(107) | $NO_2$ | Cl | $CH_2CH_3$ | $CH_3$ | $CH_3$ | navy blue |
| 10/(108) | $NO_2$ | Cl | $CH_2CH_3$ | $CH_3$ | $CH_2CH_3$ | navy blue |
| 11/(109) | CN | Br | $CH_2CH_3$ | H | $CH_2CH_3$ | blue |
| 12/(110) | CN | Br | $CH_3$ | $CH_3$ | $CH_3$ | blue |
| 13/(111) | CN | Br | $CH_3$ | $CH_3$ | $CH_2CH_3$ | blue |
| 14/(112) | CN | Br | $CH_2CH_3$ | $CH_3$ | $CH_3$ | blue |
| 15/(113) | CN | Br | $CH_2CH_3$ | $CH_3$ | $CH_2CH_3$ | blue |
| 16/(114) | CN | Cl | $CH_3$ | H | $CH_3$ | blue |
| 17/(115) | CN | Cl | $CH_2CH_3$ | H | $CH_3$ | blue |
| 18/(116) | CN | Cl | $CH_2CH_3$ | H | $CH_2CH_3$ | blue |
| 19/(117) | CN | Cl | $CH_3$ | $CH_3$ | $CH_3$ | blue |
| 20/(118) | CN | Cl | $CH_2CH_3$ | $CH_3$ | $CH_3$ | blue |
| 21/(119) | CN | Cl | $CH_3$ | $CH_3$ | $CH_2CH_3$ | blue |
| 22/(120) | CN | Cl | $CH_2CH_3$ | $CH_3$ | $CH_2CH_3$ | blue |

The preferred dyes are those of formulae (101) to (108), (110) to (113) and (117) to (120). Particularly preferred dyes are those of formulae (106), (108), (110), (117) and (119).

What is claimed is:

1. A coupling component of formula

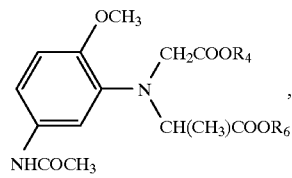

(3a)

wherein $R_4$ is methyl or ethyl, and $R_6$ is methyl or ethyl.

2. A process for the preparation of the coupling component of formula (3a) according to claim 1, which comprises reacting 3-amino-4-methoxyacetanilide first with a compound of formula $CH_3$—CHCl—$COOR_6$ and then with a compound of formula $CH_2Cl$—$COOR_4$, wherein $R_4$ is methyl or ethyl and $R_6$ is methyl or ethyl.

* * * * *